United States Patent [19]

Righter et al.

[11] Patent Number: 4,938,228
[45] Date of Patent: Jul. 3, 1990

[54] WRIST WORN HEART RATE MONITOR

[76] Inventors: William H. Righter, 540 SW 191st, Aloha, Oreg. 97006; John J. Fallin, 7680 SW 182 Pl., Aloha, Oreg. 97007

[21] Appl. No.: 311,529

[22] Filed: Feb. 15, 1989

[51] Int. Cl.$^5$ .............................................. A61B 5/02
[52] U.S. Cl. .................................... 128/690; 128/706
[58] Field of Search .............................. 128/689–690, 128/702–706

[56] References Cited

U.S. PATENT DOCUMENTS

| | | | |
|---|---|---|---|
| 3,985,121 | 10/1976 | Hellenbrand | 128/2 K |
| 4,248,244 | 2/1981 | Charnitski et al. | 128/706 |
| 4,295,472 | 10/1981 | Adams | 128/690 |
| 4,406,290 | 9/1983 | Walbeoffe-Wilson et al. | 128/689 |
| 4,420,000 | 12/1983 | Bailey | 128/706 |
| 4,456,959 | 6/1984 | Hirano et al. | 364/417 |
| 4,549,551 | 10/1985 | Dyck et al. | 128/689 |
| 4,589,420 | 5/1986 | Adams et al. | 128/702 |
| 4,732,158 | 3/1988 | Sadeh | 128/702 |

OTHER PUBLICATIONS

Allen, Douglas, "Heart-Rate Monitors: The Ideal Exercise Speedometer", Fitness Management, 34–37, (Nov./Dec. 1988).
Azevedo, Stephen and Longini, Richard L., "Abdominal-Lead Fetal Electrocardiographic R-Wave Enhancement for Heart Rate Determination", IEEE Transactions on Biomedical Engineering, vol. BME-27, No. 5, 255–260, (May 1980).
Brydon, John, "Automatic Monitoring of Cardiac Arrhythmias", 27–41.
Burke, M, J. and Whelan, M. V., "The Accuracy and Reliability of Commercial Heart Rate Monitors", Brit. J. Sports Med., vol. 21, No. 1, Mar. 1987, pp. 29–32.
Cheng, Quin-lan, and Thakor, Nitish V., "ECG Pattern Recognition by Relational Matching of Significant Points", IEEE/Eighth Annual Conference of the Engineering in Medicine and Biology Society, 288–291, (1986).
DeVel, Oliver Y., "R-Wave Detection in the Presence of Muscle Artifacts", IEEE Transactions on Biomedical Engineering, vol. BME-31, No. 11, 715–717, (Nov. 1984).
Favret, Andrew G., "Computer Matched Filter Location of Fetal R-Waves", Medical & Biological Engineering, vol. 6, 467–475, (1968).
Genaidy, A. M., Asfour, S. S. and Khalil, T. M., "An On-Line Microcomputer-Based Cardiac Monitoring System", International Journal of Industrial Ergonomics, 273–283, (1987).
Hamilton, P. S. and Tompkins, Willis J., "Quantitative Investigation of QRS Detection Rules using the MIT/BIH Arrhythmia Database", IEEE Transactions on Biomedical Engineering, vol. BME-33, No. 12, pp. 1157–1165, (Dec. 1986).
Leger, Luc, and Thivierge, Madeleine, "Heart Rate Monitors: Validity, Stability, and Functionality", The Physician and Sports Medicine, vol. 16, No. 5, May 1988.
Manning, G. K. and Dripps, J. H., "Comparison of Correlation and Modulus Difference Processing Algorithms for the Determination of Foetal Heart Rate from

(List continued on next page.)

Primary Examiner—Francis Jaworski
Attorney, Agent, or Firm—Stoel Rives Boley Jones & Grey

[57] ABSTRACT

A wrist worn heart rate monitor (100) senses a noisy biosignal with one sensor (104A) in contact with the user's finger and another sensor (104B) in contact with the user's wrist. The sensed signal is modified by a filter (112), analog to digital converter (116) and digital filter (264). A correlator (272) and QRS detector (286) are used to determine characteristics of a first segment of the modified signal. A match filter (300) and learned user reference (206) are used to match a second segment of the modified signal with the determined characteristics of the first segment to produce a processed signal. The QRS detector (286), an interval judge (292), and a momentum machine (202) determine the heart rate from the processed signal. A performance predictor (260) predicts how well the heart rate monitor (100) will perform with an individual user.

28 Claims, 7 Drawing Sheets

OTHER PUBLICATIONS

Ultrasonic Doppler Signals", Medical & Biological Engineering & Computing, 121-129, (Mar. 1986).

Monds, Fabian C. and Telford, Roger W., "Matched Filter Location of E.C.G. Complexes", Department of Electrical & Electronic Engineering, The Queen's University of Belfast, 111-118.

Pan, Jiapu and Tompkins, Willis J., "A Real-Time QRS Detection Algorithm", IEEE Transactions on Biomedical Engineering, vol. BME-32, No. 3, 230-236, (Mar. 1985).

Rodellar, Victoria, Peinado, Virginia, Gomez, Pedro and Newcomb, R. W., "MA Lattice Coefficients with Application to ECG Signal Processing", IEEE, 453-456, (Mar. 1985).

Thakor, N. V. and Webster, J. G., "Design and Evaluation of QRS and Noise Detectors for Ambulatory E.C.G. Monitors", Medical & Biological Engineering & Computing, 709-714, (Nov. 1982).

Thakor, N. V., Webster, J. G. and Tompkins, W. J., "Optimal QRS Detector", Medical & Biological Engineering & Computer, 343-350, (May 1983).

Thakor, Nitish V., "Reliable R-Wave Detection from Ambulatory Subjects", 67-72, (1978).

van Alsté, J. A. and Luursema, E. D., "Viper: A Powerful Tool for the Real-Time Calculation of Inner Products for Biomedical Signal Processing", Medical & Biological Engineering & Computing, 74-76, (Jan. 1985).

WRIST WORN HEART RATE MONITOR

TECHNICAL FIELD

This invention relates to heart rate monitors and, in particular, to a heart rate monitor that is worn on a user's wrist and determines the user's heart rate with medical grade accuracy during vigorous physical exercise.

BACKGROUND OF THE INVENTION

Muscle contraction in the human body is caused by electrical biosignals. Heart muscle contractions are caused by a biosignal referred to as the electrocardiogram (ECG) signal. The QRS complex describes a region of particular activity in the ECG signal during each heartbeat. Heretofore, various devices have been designed to determine an individual's heart rate by detecting the R-wave portion of the QRS complex.

Figure 1:
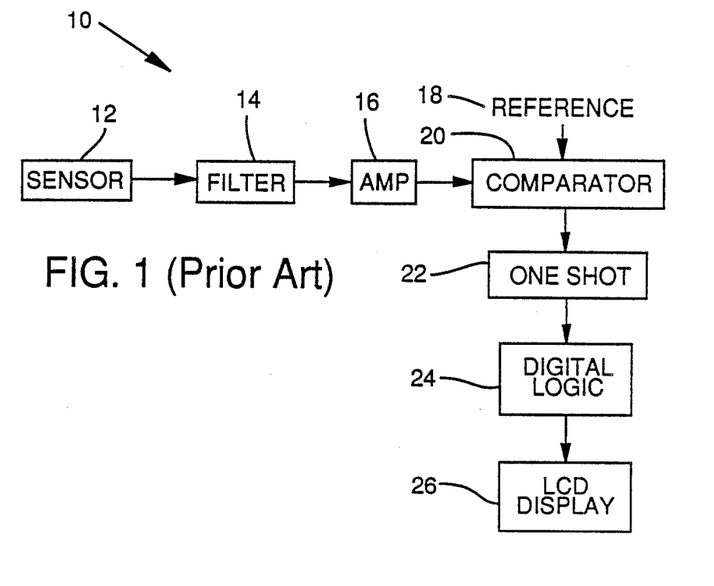
FIG. 1 is a block diagram of a prior art heart rate monitor.

These prior devices use essentially analog systems and may be described with reference to FIG. 1. Referring to FIG. 1, a conventional heart rate monitor 10 includes a sensor 12, that senses the QRS complex and accompanying noise, and a filter 14 that produces a pulse each time the QRS signal is detected. The pulse from filter 14 is amplified by amplifier 16 and compared with reference 18 by comparator 20. Whenever comparator 20 detects the proper condition, comparator 20 activates a monostable multivibrator or "one-shot" 22. Digital logic circuitry 24 produces a heart rate number to be displayed on LCD display 26 by counting the number of times one-shot 22 is activated. The combination of filter 14, amplifier 16, reference 18, comparator 20 and one-shot 22 is a analog signal processor.

Sensor 12, in the various prior devices, has been an electrode or a microphonic, piezoelectric, photo-optical or capacitive apparatus. Filter 14 has included a filter or a series of filters. Reference 18 has been a fixed voltage reference or inverse exponential voltage developed across a discharging capacitor. Comparator 20 has been a standard comparator or Schmitt trigger threshold circuit.

These primarily analog devices fail whenever the signal to noise (S/N) ratio is low. The prior systems are inaccurate because in a noisy environment they fail to detect certain signal pulses that represent heart beats, and they falsely detect noise peaks as heart beats. The weaknesses of prior devices are discussed in Leger, L., and Thivierge, M., "Heart Rate Monitors: Validity, Stability, and Functionality", *The Physician and Sports Medicine*, Vol. 16, No. 5, May 1988; and Allen, Douglas, "Heart-rate monitors: The ideal exercise speedometer", *Fitness Management*, page 34–37, Nov/Dec 1988. A low S/N ratio may be caused by at least three factors: (1) a low amplitude biosignal of the user because of skin impedance which varies from person to person when the person's skin is not properly prepared, (2) vigorous exercise by the user, and (3) poor contact between the sensor and the user.

Medical grade heart rate monitors, such as those found in hospitals, which use chest electrodes mounted onto the user's chest, and an electrode gel interface, do not ordinarily provide spurious results caused by low S/N ratio problems. In these medical grade heart rate monitors, the signal level is high because of the electrode gel and mounted electrodes, and the noise level is low because the electrodes are mounted close to the user's heart and, often, the user is not exercising while his heart rate is being measured.

Wrist worn and hand held heart rate monitors, however, are susceptible to a low S/N ratio because the inherently poor sensor contact with the user's skin provides a low signal level. Moreover, the noise level is high because the sensor is located remotely from the heart and the user is typically exercising.

SUMMARY OF THE INVENTION

Accordingly, an object of the invention is to provide a heart rate monitor that provides accurate heart rate measurement in noisy conditions where the signal is of a relatively low level and the noise is of a relatively high level.

Another object of the invention is to provide an accurate heart rate monitor that may be used with no or minimal preparation of the user's skin.

Yet another object of the invention is to provide an accurate heart rate monitor that may be worn on the user's wrist or some other location remote from the heart.

A further object of the invention is to provide a performance predictor that indicates the speed and accuracy with which the heart rate monitor of the present invention will work for the user so that the user may prepare his skin or temporarily decrease his exercising to allow the heart rate monitor of the present invention to perform quickly and accurately under more vigorous exercise conditions.

The present invention relates to a heart rate monitor that determines a user's heart rate with medical grade accuracy in noisy conditions of exercise. The heart rate monitor includes sensors that sense a noisy biosignal. The sensed signal is modified. Characteristics of a first portion of the modified signal are learned. A second portion of the modified signal is matched with the learned characteristics to produce a matched signal. The user's heart rate is calculated from the matched signal.

The invention determines the characteristics by correlating the first portion of the modified signal with prestored biosignal data to produce a correlated signal. A parametric screen and adaptive threshold are used to determine whether the correlated signal represents a QRS complex. The invention determines the user's heart rate by using the parametric screen and adaptive threshold to determine whether a certain portion of the matched signal represents a QRS complex. If it is determined that it does, then an interval judge determines whether the time intervals between QRS recognitions is consistent with what the user's heart rate should be. The interval judge outputs a counter value that represents the average interval time. A momentum machine converts counter value to rate information. The momentum machine smooths and averages the rate information and outputs it to a display.

A performance predictor determines how quickly and accurately the heart rate monitor will work with a particular user by analyzing the signal to noise ratio of the matched signal after it has been peak enhanced.

Additional objects and advantages of the present invention will be apparent from the following detailed description of a preferred embodiment thereof, which proceeds with reference to the accompanying drawings.

DETAILED DESCRIPTION OF PREFERRED EMBODIMENT

Figure 2:
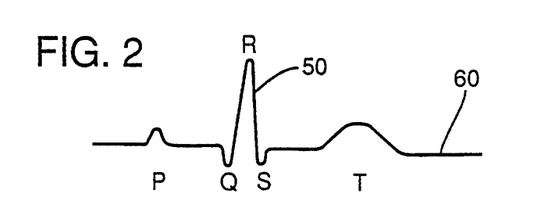
FIG. 2 is a graphical representation of a typical QRS complex region of an ECG signal.

Referring to FIG. 2, a typical QRS complex 50 is shown on biosignal 60. Biosignal 60 is typical of an electrocardiogram ("ECG") signal detected from a person's chest by using a standard 3-LEAD ECG cardiograph instrument and chest electrodes mounted onto prepared skin. Skin is prepared by rubbing an abrasive over the skin to remove dead skin and/or by applying electrode gel to the skin. Q, R, and S designate sections of the QRS complex. P and T designate particular activity in biosignal 60 before and after the QRS complex. The QRS complex varies from person to person, but normal QRS complexes do not vary significantly from heart beat to heart beat in the same person. As the heart beat of a person increases or decreases, the time between QRS complexes decreases and increases, respectively.

For ease of description, biosignal 60 will represent both a typical noise-free biosignal and the noise-free biosignal of a hypothetical user described in connection with FIGS. 3, 5, 6A, and 6B. Likewise, the signals shown in FIGS. 4A and 4B represent both a typical preprocessed and processed biosignal, and a preprocessed and processed biosignal of a hypothetical user described in connection with FIGS. 3, 5, 6A, and 6B, with signal pickup at the wrist and fingers without skin preparation.

HARDWARE

Figure 3:
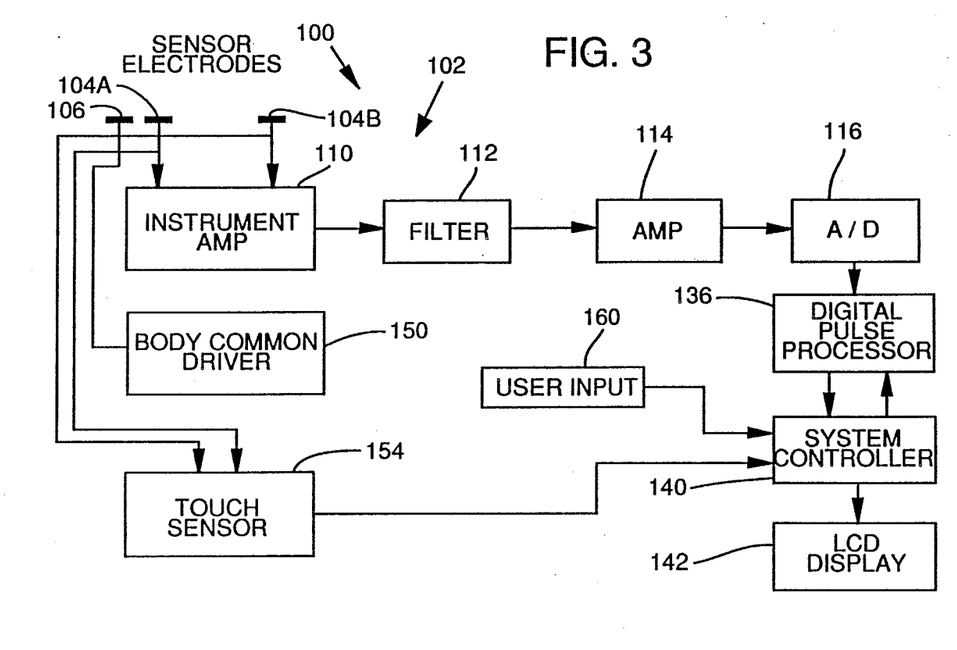
FIG. 3 is a block diagram of the hardware used in the present invention.
Figure 4A:
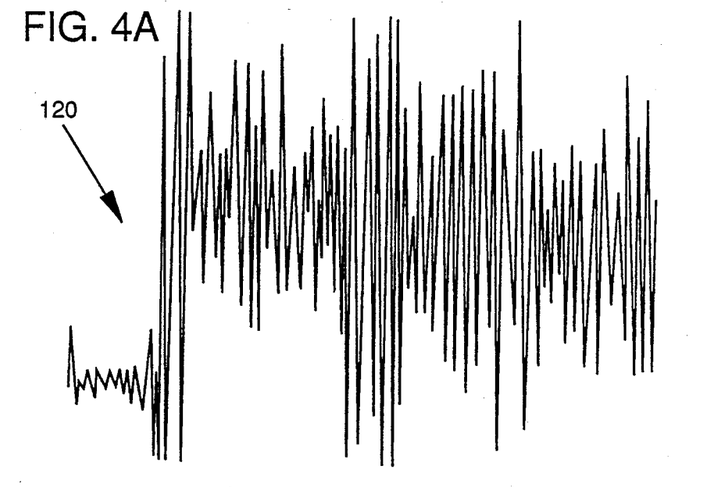
FIG. 4A is a graphical representation of actual data of a typical biosignal before it is processed by the signal processing procedures of this invention.
Figure 4B:
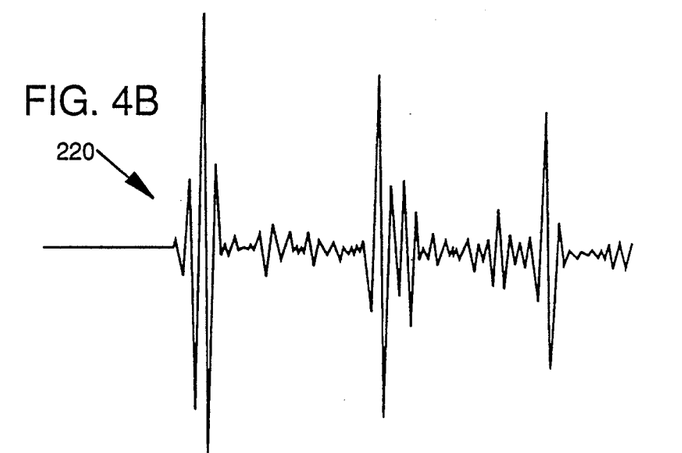
FIG. 4B is a graphical representation of actual data of a typical biosignal after it has been processed by the signal processing procedures of this invention.

Referring to FIG. 3, a preferred embodiment of wrist worn heart rate monitor 100 includes hardware apparatus 102. Hardware apparatus 102 includes electrode sensors 104A and 104B. Sensors 104A and 104B convert biosignal 60 mixed with noise into a corresponding electric signal by converting ions at the user's wrist and finger to electronic charge in sensors 104A and 104B. Sensors 104A and 104B are electrically connected to the differential inputs of instrument amplifier 110.

Heart rate monitor 100 is designed to be worn as a wrist watch with sensor 104B in contact with the user's wrist. To operate heart rate monitor 100, a finger from the opposite hand is placed in contact with sensor 104A. For example, if the left wrist is used, a finger from the right hand is used.

Heart rate monitor 100 is not limited to being used with a wrist and finger. It may be used with any two parts of the body having opposite polarity. For example, three other combinations that may be used are the forehead and a finger on the left hand, both feet, and fingers from the right and left hands. Therefore, whenever this application refers to the user's wrist and finger, it is apparent that other parts of the body could be substituted.

Further, while sensors 104A and 104B are electrodes in the preferred embodiment, they may be any other type of sensor that detects a biosignal, for example, a microphonic, piezoelectric, photo-optical or capacitive sensor. Such sensors may be of the type described in United States Patent No. 4,295,472 of Adams (electrode); U.S. Pat. No. 4,181,134 of Mason et al. (electrode); U.S. Pat. No. 4,436,096 of Dyck et al. (microphonic); U.S. Pat. No. 4,549,551 of Dyck et al. (microphonic); U.S. Pat. No. 4,195,642 of Price et al. (piezoelectric); U.S. Pat. No. 4,202,350 of Walton (piezoelectric); U.S. Pat. No. 4,224,948 of Cramer et al. (photo-optical); U.S. Pat. No. 4,301,808 of Taus (photooptical); and U.S. Pat. No. 4,248,244 of Charnitski (capacitive). A silver chloride electrode is preferred.

The noise mixed with biosignal 60 includes electrical noise sources, such as common 60 Hertz, tribo electrical noise from cable flexing; machine generated noise such as electromagnetic noise from exercising equipment; and artifact noise from mioelectric muscle artifact, and surface artifact at the electro-skin contact.

The corresponding signal from sensors 104A and 104B is amplified by instrument amplifier 110 and filtered by filter 112. Filter 112 is an analog band pass filter centered around 12 Hz with a band width of 6 Hz. Filter 112 limits the frequency components of biosignal 60 mixed with noise so as to satisfy the Nyquist sampling criterion when these signals are digitized. Filter 112 also band limits low frequency noise. The filtered corresponding signal is amplified by amplifier 114 and digitized by analog to digital converter (A/D) 116. The output from A/D 116 is preprocessed signal 120 shown in FIG. 4A.

Preprocessed signal 120 includes three QRS complexes associated with three heartbeats, and noise. Preprocessed signal 120 is representative of the signals that conventional heart rate monitors can produce without the use of gels in making skin contact during exercise. FIG. 4A shows a representation of actual test data of preprocessed signal 120 of heart rate monitor 100.

Preprocessed signal 120 is processed by digital pulse processor 136, in order to determine the user's heart rate. Digital pulse processor 136 includes a microprocessor that is controlled by system controller 140, which also includes a microprocessor. The microprocessor in digital pulse processor 136 may be an Intel 80C96 or 80C51. The software language used to program the Intel 80C96 and 80C51 may be PLM, which is similar to PL1. The microprocessor used in system controller 140 may be an NEC 7503. The NEC 7503 may be programmed in machine specific assembly language.

The value of the heart pulse rate is displayed on LCD display 142. LCD display 142 also includes a flashing heart shaped indicator that flashes at the rate of the heart rate. In addition, LCD display 142 includes information from a performance predictor that will be described in connection with FIGS. 5 and 6B.

Ground element 106 is electrically connected to body common driver 150. Body common driver 150 is an actively driven ground reference that is isolated to protect the user against electrical shock. Ground element 106 is in close proximity to sensor 104A, such that the finger used to touch sensor 104A will also touch ground 106. Whenever heart rate monitor 100 is used in a wrist-worn configuration, it is preferable to not have a ground in close proximity to sensor 104B because perspiration from the user's wrist would tend to short out sensor 104B. In other embodiments, such as an exercise bike handle bar-mounted sensor, a ground element is preferably used in connection with both sensors 104A and 104B, since the ground and sensor may be spaced sufficiently far apart to avoid shorting the sensors.

When a photo-optical system is used, sensor 104A would be a light source and sensor 104B would be a light detector, with the user's skin placed between the light source and light detector. If a photooptical system is used, ground 106 is not needed. When a microphonic or piezoelectric system is used, no electrical ground 106 is required. When a capacitive detection system is used, sensor 104A could be a dielectric thin films coated metal plate and sensor 104B could be ground. A separate ground 106 may be needed. In the preferred embodiment, electrode sensors 104A and 104B differentially pick up two different aspects of the same biosignal. Alternatively, if a microphonic, piezoelectric, photooptical or capacitive sensor is used, then there would not be a differential input unless more than one sensor of a type is used, e.g., an array a photooptical sensors.

Sensors 104A and 104B are electrically connected to touch sensor 154. Touch sensor 154 is an analog signal processor with a comparator that outputs a logic one state to system controller 140 whenever both the user's finger is in contact with sensor 104A and wrist is in contact with sensor 104B. Touch sensor 154 outputs a logic zero otherwise.

User input 160 allows the user to select the mode of operation of heart rate monitor 100 through system controller 140. Available modes include time of day, stop watch and pulse mode. Pulse mode initiates a pulse read function that determines the heart rate. Pulse mode is divided into three modes: learning mode, operating mode, and intermediate mode. During learning mode, the characteristics of the user's QRS complex are learned. During operating mode, the learned characteristics are used in determining the user's heart rate. During intermediate mode, the learned characteristics are stored, but not utilized.

Learning mode is initiated when sensor 154 is in the logic one state following the user's selection of pulse mode. Learning mode is concluded whenever the characteristics have been learned, or either pulse mode ceases to be selected or touch sensor 154 returns to the logic zero state before the characteristics have been learned. Operating mode occurs whenever the characteristics have been learned and retained in storage, pulse mode is still selected, and touch sensor 154 is in the logic one state. If the user continuously touches sensors 104A and 104B at the end of learning mode, then heart rate monitor 100 will go straight from learning mode to operating mode. Intermediate mode occurs whenever the characteristics have been learned and retained in storage, pulse mode is still selected, and touch sensor 154 is in the logic zero state. It is contemplated that the user will switch back and forth between intermediate mode and operating mode.

PROCEDURAL OVERVIEW

Figure 5:
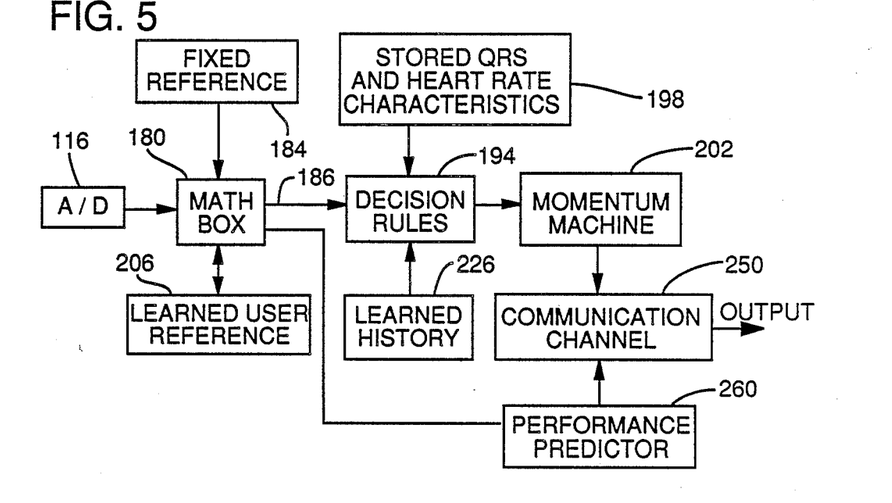
FIG. 5 is an architectural block diagram showing in outline form the procedures carried out in the digital pulse processor of the present invention.

FIG. 5 is an architectural block diagram representation that provides an overview of the procedures performed by digital pulse processor 136. When the user wishes to begin determining his heart rate, he wears heart rate monitor 100 so that his wrist is touching sensor 104B, selects pulse mode on user input 160, and touches sensor 104A and ground 106 with his finger. System controller 140 then initiates the pulse read function.

With digital pulse processor 136 in learning mode, math box 180 receives preprocessed signal 120 from A/D 116. Math box 180 attempts to maximize the S/N ratio of preprocessed signal 120 and enhances signal peaks through a nonlinear transform. Math box 180 is a series of digital signal processing algorithms. The algorithms performed by math box 180 may be implemented in digital pulse processor 136 or in separate hardware.

Math box 180 determines the characteristics of the user's individual QRS complex 50 by correlating preprocessed signal 120 with a standard QRS complex representation that is stored in fixed reference 184. The output from math box 180 is received through connector 186 by decision rules box 194. Decision rules box 194 is a series of decision trees that determine whether the output of math box 180 contains a segment that represents a QRS complex. If it is determined that a segment does represent a QRS complex, then that segment is stored in learned user reference memory 206.

Once five segments representing the user's QRS complexes are stored in learned user reference 206, an average of the five segments is made. A template of the average is made and retained in learned reference 206. The template represents the user's QRS complex. Digital pulse processor 136 then switches from learning mode to operating mode (although digital pulse processor 136 may have been in intermediate mode and thus have gone from intermediate mode to operating mode).

In operating mode, digital pulse processor 136 determines the rate of QRS complexes from preprocessed signal 120. Math box 180 matches preprocessed signal 120 with the user's QRS characteristics, i.e., the average QRS complex template in learned reference 206, to maximize the S/N ratio of preprocessed signal 120. The output of math box 180 on connector 186 is processed signal 220, shown in FIG. 4B. Processed signal 220 is substantially cleaner than preprocessed signal 120.

Processed signal 220 is received by decision rules box 194. Decision rules box 194 determines whether particular segments of processed signal 220 represent a heart beat. Decision rules box 194 compares processed signal 220 with stored information in stored QRS and heart rate characteristics registers 198 and information related to the user's current heart rate in learned history register 226.

The output from decision rules box 194 is received by momentum machine 202. Momentum machine 202 calculates the variable depth or weighted moving average ECG frequency based on past and present ECG intervals. Special techniques which are described in the procedural details section of this application are used to smooth the data for a steady display. If the heart rate is very high, then it is important to detect rapid changes in the heart rate, and momentum machine 202 will respond accordingly by using fewer samples in its average. If the rate is slow, then the user probably does not demand quick response time. In this case, momentum machine 202 gives a slower, smoother response by using more samples in its average. Communications channel 250 receives the result from momentum machine 202 and outputs it to LCD display 142 through system controller 140.

The ability of heart rate monitor 100 to determine an accurate heart beat rate depends on three factors. The first factor is the signal to noise ratio of the biosignal at the skin of the user. This ratio varies from person to person. The second factor is the vigorousness with which the user is exercising. More vigorous exercising causes greater noise and thus decreases the signal to noise ratio. The third factor is the quality of the contact between the skin of the user and sensors 104A and 104B. A higher quality contact reduces the skin impedance thus allowing a greater signal to be sensed by sensors 104A and 104B.

If one of the three factors is particularly low, heart rate monitor 100 may still work if the other two factors are high. For example, if user's S/N ratio is low, then the user could decrease the level of exercise or increase the quality of the skin-sensor contact. The quality of the skin-sensor contact may be increased by preparing the skin with an abrasive or using electrode gel.

Heart rate monitor 100 includes a performance predictor 260. Performance predictor 260 operates only during learning mode. Performance predictor 260 provides a performance number between 0 and 7 that is displayed on LCD display 142. The performance number indicates the signal quality of the user's processed signal 220. The performance number predicts how well heart rate monitor 100 will perform for the particular user under the noisy condition of exercise, i.e., how quickly heart rate monitor 100 can determine the user's heart rate during typical exercise conditions. The lower the performance number, the more quickly heart rate monitor 100 can determine the user's heart rate during a given exercise activity, or alternatively what amount of exercise activity can be tolerated while maintaining reasonable read times. In addition, with a high performance number, heart rate monitor may require more samples to determine the heart rate in operating mode.

Heart rate monitor 100 provides medical instrument grade accuracy through applying sensor electrodes 104A and 104B to the user's wrist or fingers. Heretofore, medical instrument grade accuracy was only achievable through the use of medical equipment including chest leads, electrode gel or paste, and medical electrodes. Medical instrument grade accuracy is defined in the Association for the Advancement of Medical Instrumentation AAMI Standards and Recommended Practices 1987, Reference Book, paragraph 3.2.7, section EC13:

3.2.7 Range and Accuracy of Heart Rate Meter. The minimum allowable heart rate meter range shall be 30 to 200 bpm, with an allowable readout error of no greater than ±10 percent of the input rate or ±5 bpm, whichever is greater. Cardiac monitors labeled for use with pediatric patients shall have an extended heart rate range of at least 250 bpm. In addition, input ECG signals at rates less than the disclosed lower limit of the rate meter range shall not cause the meter to indicate a rate greater than this lower limit. Input signals at rates above the disclosed upper limit of the rate meter range, up to 300 bpm (350 bpm for monitors labeled for use with pediatric patients), shall not cause the meter to indicate a rate lower than this upper limit.

PROCEDURAL DETAILS

Figure 6A:
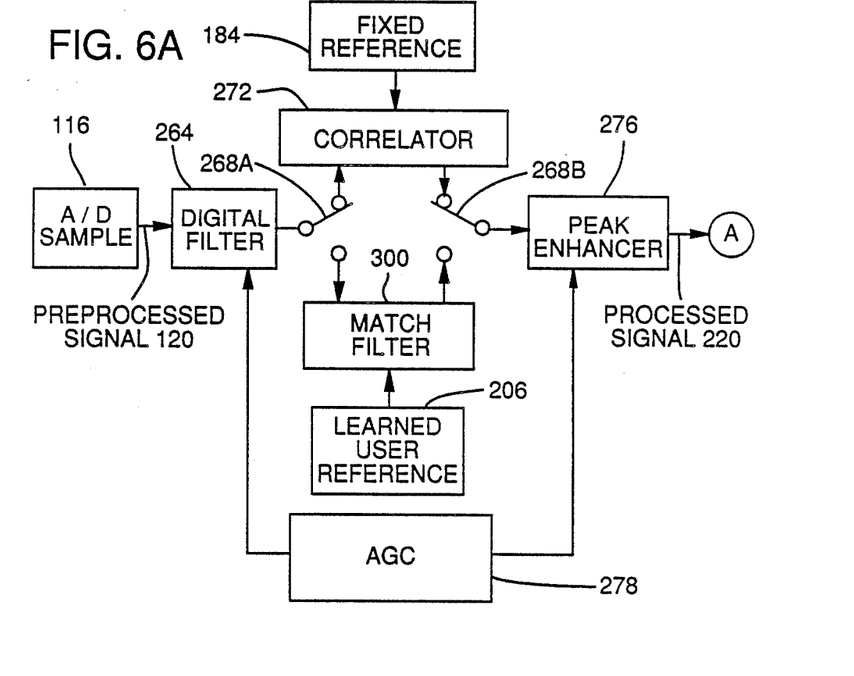
FIGS. 6A and 6B are detailed architectural block diagrams of the procedures carried out in the digital pulse processor of the present invention.
Figure 6B:
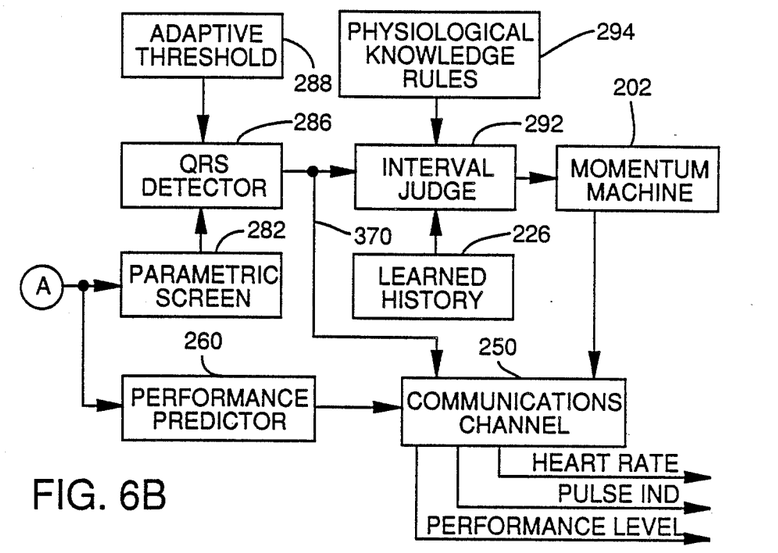

FIGS. 6A and 6B show a more detailed representation of the procedures that are included in FIG. 5. FIG. 6A shows the procedures of FIG. 5 that occur before processed signal 220 is received by decision rules box 194. FIG. 6B shows the procedures of FIG. 5 that occur after processed signal 220 has been received by decision rules box 194. Referring to FIG. 6A, preprocessed signal 120 is received by digital filter 264 from A/D 116. Digital filter 264 is a band pass filter centered at 12 Hz with a band of about 6 Hz. Digital filter 264 may be recursive or nonrecursive.

Referring to learning mode, when heart rate monitor 100 is first used, switches 268A and 268B are connected to cross-correlator 272. Cross-correlator 272 is a fixed reference correlator implemented using integer arithmetic, although floating point arithmetic may be alternatively used. Fixed reference 184, as explained in connection with FIG. 5, is a numerical representation of a standard QRS complex. Fixed reference 184 may have from 16 to 32 data points, depending on the data sampling rate.

Cross-correlator 272 receives an incoming bit stream from digital filter 264 and correlates the entire bit stream as each new bit is received. The output of cross-correlator 272 is a maximum peak whenever the incoming bit stream correlates closest with the contents of fixed reference 184. Cross-correlator 272 takes the sum of the bits multiplied by a corresponding value from fixed reference 184 as described by equation 1 below:

$$y(n) = \sum_{n=0}^{d} C_n * x(n - d), \tag{1}$$

where y is the output of cross-correlator 272, C is one of n coefficients from fixed reference 184, and x is a particular sample of the signal from digital filter 264. The parameter d represents the number of datapoints and is between 16 and 32.

Peak enhancer 276 performs a nonlinear transform on the signal from cross-correlator 272 according to equation 2 below:

$$f(x) = |x|^n sign(x) \tag{2}$$

where n is an empirically chosen constant of between 1.6 and 2.0. The absolute value of x is raised to the power n. In order to retain the original signal of x, $|x|^n$ is multiplied by the sign of x. The value of n is preferably chosen to be 2.0 for simplicity and efficiency in real-time computing. However, other values may be more optimal where the signal peaks received by peak enhancer 276 vary broadly in amplitude. Alternatively, the constant n could be an adaptive variable that is set under control of performance predictor 260 to allow optimization if the sample rate is too low or if QRS complex 50 is strongly modulated by a respiration wave.

The purpose of peak enhancer 276 is to further increase the numerical value of the peaks of the signal from cross-correlator 272, thus accentuating the difference between the signal peaks and the noise. The output of peak enhancer 276 is processed signal 220, shown in FIG. 4B. Symbol A connects FIG. 6A to FIG. 6B.

An automatic gain control AGC 278 may be used with heart rate monitor 100 when floating point arithmetic is used. AGC 278 may be used with an autoscaler and overflow detection when integer arithmetic is used. Adaptive threshold 288 performs an equivalent function to AGC 278. AGC 278 sets a gain range and adaptive threshold 288 works within that range.

Processed signal 220 is received by parametric screen 282. Parametric screen 282 is activated and begins its measurement process when an internal state machine determines that the incoming waveform data stream has transitioned through a local minimum turning point followed by a local maximum turning point, followed finally by a local minimum turning point. Waveform alignment occurs at the last turning point and parametric screens are applied. This alignment point will become the point of detection if the waveform passes the parametric screen and meets requirements of adaptive threshold 288. Parametric screen 282 is a decision tree that determines whether processed signal 220 has slopes, widths, and amplitudes that are within standard ranges as will be explained in connection with FIG. 7.

Figure 7:
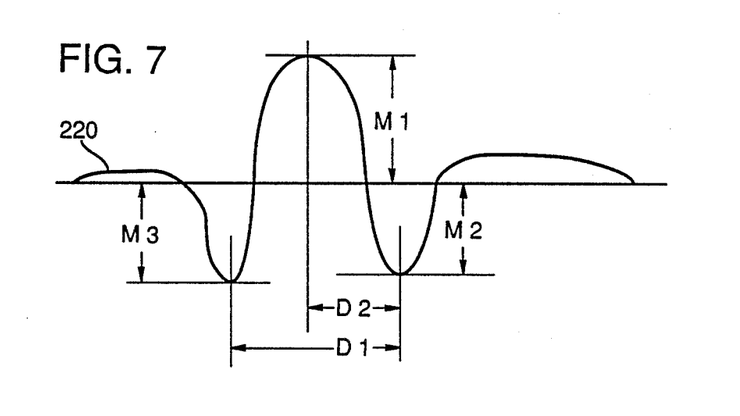
FIG. 7 is an illustration of the measurement of certain parameters used in the present invention.

FIG. 7 shows a portion of processed signal 220 that represents a QRS complex that has been received by parametric screen 282. Parametric screen measures processed signal 220 at certain points to determine $D_1$, $D_2$, $M_1$, $M_2$, and $M_3$ as are shown in FIG. 7. If any of these parameters is not within the prestored standard range, then a signal is not output from parametric screen 282. Alternatively, if one or more of these parameters narrowly miss the range, but other parameters are within the range, parametric screen 282 could allow processed signal 220 to pass.

If processed signal 220 does not meet the requirements of parametric screen 282, then it does not advance further in heart rate monitor 100. If processed signal 220 meets the requirements of parametric screen 282, then it is subject to the requirements of adaptive threshold 288.

Figure 8:
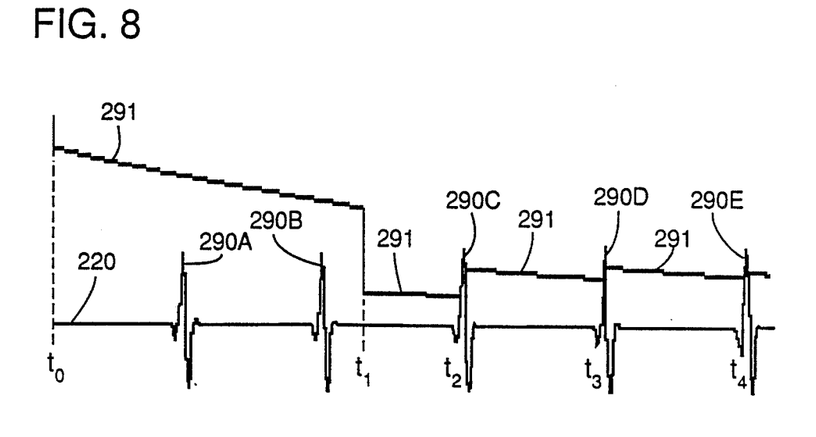
FIG. 8 is an illustration of the processed signal and the threshold signal of the adaptive threshold of the present invention.

Adaptive threshold 288 contributes to the accuracy of heart rate monitor 100 by reducing the number of false positive or false negative detects that occur. A false positive detect occurs when a heart rate monitor determines that a portion of a signal represents an R-wave of a QRS complex when in fact it does not. A false negative detect occurs when the detector fails to fire when a valid R-wave is present. Prior art hardware techniques use a fixed reference threshold or a negative exponential decaying voltage on a capacitor. The software thresholding techniques used by adaptive threshold 288 reduce errors by applying adaptive algorithms to peaks in the signal from parametric screen 282. The algorithms used in adaptive threshold 288 are explained in connection with FIG. 8 and equation 3 below:

$$\text{Threshold} = k * 1/n * \sum_{i=1}^{n} (\text{R-wave-peak}[n - i]) * e^{-\lambda T}, \quad (3)$$

where $0.6 \leq k \leq 0.75$ depending on the average noise level, $\lambda$ is the inverse of the time constant (e.g., 4 or 5 seconds) divided by the data sample rate (e.g., 125 samples/second). T is the number of samples since the last QRS detection, R-wave-peak is the magnitude of the R wave in the QRS signal and n is the size of the array that stores R-wave-peak values. A time constant of 4 seconds and sample rate of 125 samples/second would result in $\lambda = 0.002$. However, $\lambda$ may be 0.001955 for programming ease since the PL1program implements $e^{-\lambda t}$ as a shift operation.

FIG. 8 shows processed signal 220 and QRS complexes 290A–290E. Threshold 291 is shown from time $t_0$ to time $t_4$. At time $t_0$, threshold 291 is initialized to its starting value. Threshold 291 falls according to equation 3. If a detection has not occurred within two seconds, then threshold 291 is set to k multiplied by the largest peak that has occurred within the last 2 seconds. Time $t_1$ occurs 2 seconds after time $t_0$. However, if a peak crosses threshold 291 during the first two seconds, then threshold 291 is set to k multiplied by that peak. Subsequently, each time a valid QRS complex is detected at times $t_2$, $t_3$ and $t_4$, threshold 291 is reset to k multiplied by the average of last n peaks. Alternatively, the threshold may be set to the median value of the last n peaks to provide a marginal improvement in the detector error rate, as is described in Hamilton, P.S. and Tompkins, W.J. "Quantitative Investigation of QRS Detection Rules using the MIT/BIH Arrhythmia Database", *IEEE Transactions on Biomedical Engineering*, No. 12 (December, 1986).

For computational efficiency the preferred embodiment has a four point mean with a four to five second time constant decay on a negative exponential. QRS detector 286 outputs a pulse having a width of one data sample time (i.e., if the sample rate time period of A/D convertor 116 is 8 ms, the pulse width is 8 ms), with the pulse beginning at the last turning point (point of alignment in parametric screen 282) of the incoming waveform.

QRS detector 286 fires if the R-wave portion of the QRS complex exceeds the value of adaptive threshold 291. QRS detector 286 also fires if the conditions of the respiration rule are met. The respiration rule is defined by the following decision algorithm: QRS detector 286 fires if (1) a waveform passes parametric screen 282, (2) the R-wave of the waveform does not exceed threshold 291, but does exceed one-half the value of threshold 291, and (3) the R-wave occurs within a window where a QRS is expected.

The modulation of R-wave amplitudes by respiration is known and has been treated with a dual threshold technique. Dual thresholding techniques are described in Pan, J., and Tompkins, W.J. "A real-time QRS Detection Algorithm", *IEEE Transactions on Biomedical Engineering*, No. 3 (March 1985). Heart rate monitor 100 improves upon prior methods of dual thresholding by applying parametric screen 282 and a window of expectance in addition to the dual thresholding to detect QRS complexes whose R-waves would not exceed the detection threshold due to deep breathing or heavy respiration, which is common during exercise activity.

The output of QRS detection box 286 is a series of pulses. Each pulse represents a detected QRS complex. After the QRS detector has fired, there immediately follows a 200 ms blanking period wherein the QRS detector cannot fire again. This blanking period discriminates against false triggering of the detector primarily by large T-waves, and also filter ringing or any large noise bursts. This advantageous blanking period is possible because of the physiological rule that T-waves will always occur within 200 ms of a QRS complex, and a subsequent QRS complex will never occur within 200 ms of the previous one.

Interval judge 292 determines whether the pulses actually represent QRS complexes by measuring the intervals between them. To do this, interval judge 292 uses information from physiological knowledge rules registers 294. Physiological knowledge rules registers 294 includes information that consecutive human heart beat intervals do not vary by more than about 12.5% (one-eighth) from adjacent intervals and the human heart rate is between 30 and 220 beats per minute.

As described above, heart rate monitor 100 operates in three modes: learning mode, operating mode, and intermediate mode. Operating mode includes two submodes: first read mode and continuous read mode. Interval judge 292 performs the same procedures whether in learning mode or first read mode to prepare interval judge 292 for continuous mode. In both learning mode and first read mode, interval judge 292 determines whether acceptable pulse intervals have been received by interval judge 292 from QRS detector 286 and computes the average value of those intervals. This average value is then stored in learned history register 226 to be used by interval judge 292 during continuous read mode.

If the user keeps his finger on sensor 104A following the conclusion of learning mode, then heart rate monitor 100 will go directly from learning mode to continuous read mode in operating mode. If, however, heart rate monitor 100 is in intermediate mode before the user touches sensor 104A, then the information stored in learned history register 226 will no longer be current and it will have to be updated by interval judge 292 in first read mode, before interval judge 292 will perform in continuous read mode.

Figure 9:
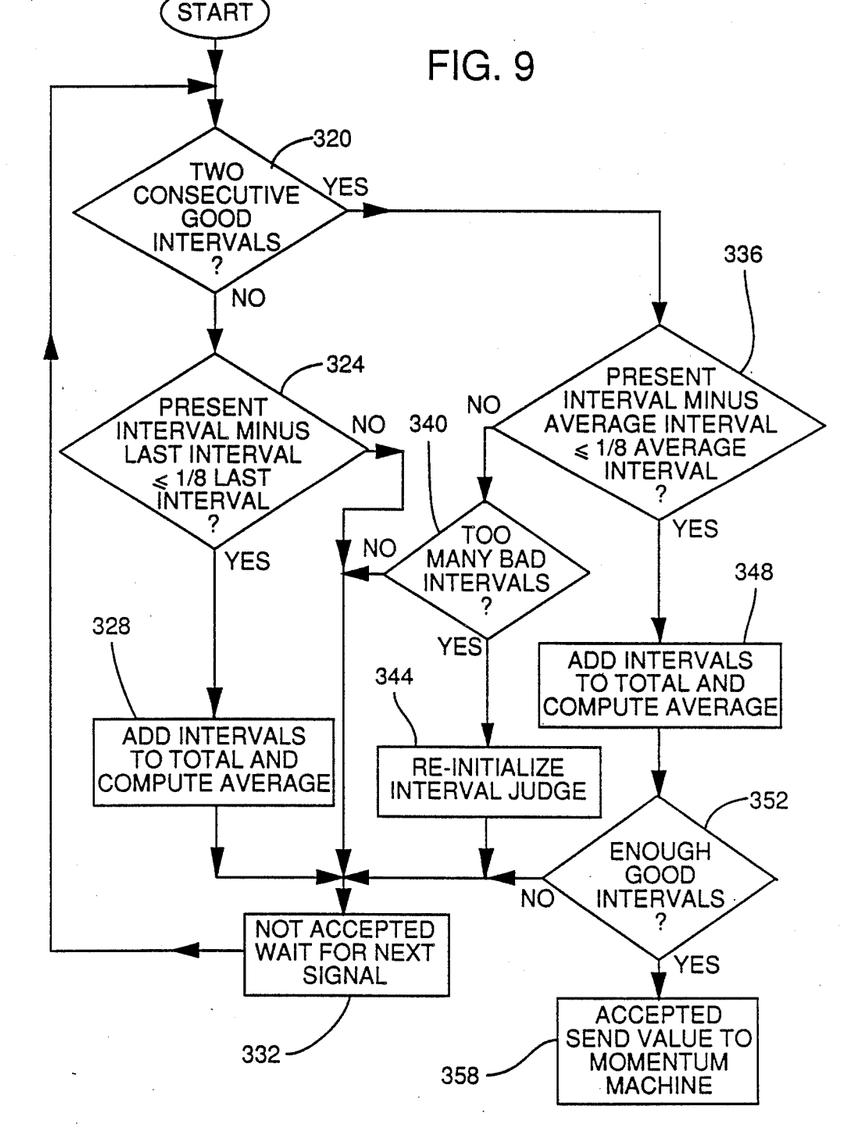
FIG. 9 is a flowchart of procedures used in the interval judge of the present invention.

FIG. 9 is a flow chart of procedures performed by interval judge 292. Decision box 320 represents a determination of whether two consecutive good intervals have been detected. An interval is the distance in time between two consecutive output pulses of QRS detector 286. An interval is determined by a counter incremented at the sample rate that starts at the first pulse from QRS detector 286, and is read and reset on the second pulse.

Good intervals can be detected only by a comparison with a previous interval, as represented in decision box 324. The present interval is a good interval if the difference between the present interval and the last interval is less than or equal to one eighth of the last interval, as represented in decision box 324. In addition, a good interval falls within the range of 30 to 220 heart beats per minute. The present interval is added to the intervals previously determined and an average is computed, as represented in operation box 328. Interval judge 292 waits for the next signal from QRS detector 286, as represented in operation box 332.

While still in learning mode or first read mode, if two consecutive good intervals are detected, then the answer to decision box 320 is "yes", and interval judge 292 then matches the next series of intervals with the average of the two "good" intervals to determine whether there are two more good intervals before there are two bad intervals. It is determined whether the difference between the present interval and the average of intervals already detected is less than or equal to one eighth of that average interval, as represented in decision box 336. If the difference is not less than or equal to one eighth, then the interval is discarded and the bad interval count is increased by one.

It is then determined whether there have been too many bad intervals, as represented in decision box 340. In learning mode and first read mode, two bad intervals is too many. If there have been too many bad intervals, then interval judge 292 is reinitialized as represented in operation box 344, and interval judge 292 waits for the next signal from QRS detector 286. If there have not been too many bad intervals, then interval judge 292 merely waits for the next signal.

If the answer to decision box 336 is yes, then the present interval is added to the total of the intervals previous determined and an average is computed, as represented in operation box 348. Decision box 352 represents a determination of whether enough good intervals have been detected by decision box 336. In learning mode and first read mode, two good intervals is enough. If there have not been enough good intervals, then interval judge 292 waits for the next signal. If there have been a sufficient number of good intervals, then heart rate monitor 100 is switched to continuous read mode.

Interval judge 292 performs in the same manner in continuous read mode as it does in learning mode and first read mode except as explained below. In continuous read mode, the answer to decision box 320 is always yes. The average interval in decision box 336 comes from learned history 226, which obtained the average from operation box 348. In continuous read mode, six bad intervals are too many, as asked by decision box 340. Four or seven good intervals are a sufficient number as asked by decision box 352. Four good intervals are sufficient if the user's heart rate is less than or equal to 128 beats per minute. Seven good intervals are sufficient if the user's heart rate is greater than 128 beats per minute. Each time a sufficient number of good intervals are received, the average of the intervals is sent to momentum machine The purpose of having a variable number of required good intervals is (1) to provide a relatively constant read time regardless of heart rate and (2) under very noisy conditions to accumulated many intervals to reduce probability of accepting noise burst as good intervals. Of course, the required number of good intervals could be other than four and seven.

Interval judge 292 passes interval period information to momentum machine 202. The output of interval judge 292 is a counter value of the average time interval of the last four or seven good intervals.

Momentum machine 202 changes the counter period information to pulse rate information and smooths and averages the rate information according to equation 4 below:

$$\text{heart rate} = \sum_{i=0}^{n} k_n * P(n - i), \quad (4)$$

where P is an array of depth n, and $k_n$ is a weighted or unweighted coefficient. If $k_n$ is an unweighted coefficient, then n is a variable depth value. If $k_n$ is a weighted coefficient, then n is a constant depth value. $k_n$ is $1/n$ if it is unweighted. Momentum machine 202 could include both a weighted coefficient $k_n$ and a variable depth array, but it would be redundant.

When the user's heart rate is changing rapidly (e.g., during exercise warm-up or cool down) the coefficient values, which are normally equal, are changed to weight more heavily the most recent heart rate values.

Alternatively, the array size, which is normally eight is changed to four. In this way, the rapidly changing heart rate is reflected in a more quickly changing moving average, with the LCD display 142 accurately tracking the changing heart rate.

During learning mode, momentum machine 202 is initialized. If heart rate monitor 100 goes directly from learning mode to operating mode, then momentum machine 202 will not need to be reinitialized, and heart rate monitor 100 will go directly to continuous read mode in operating mode. If, however, heart rate monitor 100 goes from intermediate mode to continuous mode, then momentum machine 202 will need to be reinitialized through first read mode.

Performance predictor 260 produces performance predictor levels to indicate the signal quality of the user's processed signal 220. Performance predictor levels 0 and 1 indicate that heart rate monitor 100 will provide accurate readings with fast learn times under vigorous exercise conditions. Approximately 50% of population fit into this category. Performance predictor levels 2 and 3 indicate that the user may have to prep his skin or reduce his exercise activity (e.g., reduce from running to slow jog) to receive a heart rate reading within a reasonable time (3–12 sec.). Approximately 35% of population fit into this category. Performance predictor levels 4 and 5 indicate that the user will probably have to stop exercising to get a heart rate reading. Approximately 15% of the population falls into this category. Levels 6 and 7 are not used and constitute a signal gain that is so high that heart rate monitor 100 does not detect any signal at all.

One of the purposes of performance predictor 260 is to provide advanced information to a potential user so that he may gauge the usefulness of heart rate monitor 100 in his physical activity. For example, with a performance predictor level of 3–5, a user can be instructed to prep his skin first with moisture or by buffing the skin surface to reduce the skin-electrode impedance, and thus improve unit performance during exercise. Or, at a point of purchase a potential user can decide what level of exercise activity can be sustained while still getting accurate heart rate of information. A person that receives a level 5 will know in advance that his inherent biosignal has too poor quality to detect during exercise. He would not otherwise know this without performance predictor 260.

The accuracy of performance predictor 260 is based on unpublished data gathered during a study conducted by Ralin, Inc., assignee of the present application. The relevant conclusions of this study are included in this detailed description of the preferred embodiment of the present invention. The data taken on 40 adults included the individual performance predictor value taken at rest. The heart rate read out of heart rate monitor 100 was recorded simultaneously with two separate ECG machines under increasing exercise activities (e.g. sitting, walking, biking, jogging and running). A linear regression and correlation analysis showed a very high degree of correlation between predicted unit performance as estimated by performance predictor 260 and actual measurements of accuracy during exercise. Performance is defined based on both accuracy under exercise and learn time.

The performance predictor may work in the following manner: At the end of the learning mode or first read mode, a measure of the peak R-wave signal is divided by the average noise to determine the signal-to-noise ratio. The average noise is determined by subtracting the detected QRS wave from the incoming data, i.e., noise. The signal to noise ratio is divided into the first learning time (in seconds) and normalized so that the final values fall between 0 and 7. The first learning time is the time required for heart rate monitor 100 to complete the learning process for the first time.

A simplified alternative method, which may be used for computational efficiency, is to assign, through a look-up table or algorithmic means, a performance predictor level number to each of eight different amplitude ranges. For example:

if R-wave-peak $>0$, then performance predictor $=7$
if R-wave-peak $>400$, then performance predictor $=6$
if R-wave-peak $>900$, then performance predictor $=5$
if R-wave-peak $>2500$, then performance predictor $=4$
if R-wave-peak $>4900$, then performance predictor $=3$
if R-wave-peak $>8200$, then performance predictor $=2$
if R-wave-peak $>12100$, then performance predictor $=1$
if R-wave-peak $>16000$, then performance predictor $=0$, where the maximum value is 16384. Using equation 2, $x^n = 16384$, where $x=128$ and $n=2$. 128 is the maximum positive digital voltage level on the transformed R-wave.

The characteristics of the user's QRS complex that are determined in learning mode are stored in learned user reference 206, shown in FIG. 6A. Learned user reference 206 contains a template of coefficients of the user's QRS complex. The template is produced in learning mode as follows and does not need to be relearned as long as heart rate monitor 100 is in pulse mode. The output of digital filter 264 is stored in a register (not shown). Whenever QRS detector 286 fires, the last n samples in the register, which represent a QRS complex, are stored in learned user reference 206. The register then receives another group of samples from digital filter 264 When QRS detector 286 fires, an average is made of the samples from the register and the samples in learned user reference 206. The average is stored in learned user reference 206. This is repeated until the contents of learned user reference 206 is the average of five QRS sample groups from the register. A template is made of the average and stored in learned user reference 206. Of course, the template could be made of an average of fewer than five QRS sample groups, or from just one QRS sample group.

A preferred way to use heart rate monitor 100 is to take the first heart rate reading at rest so as to store the cleanest possible signal in learned user reference 206 while heart rate monitor 100 is in learn mode.

Referring to FIG. 6A, switch 268A and 268B are connected to match filter 300 as heart rate monitor 100 switches from learning mode or intermediate mode to operating mode. Match filter 300 is a sample reference correlator implemented using integer arithmetic. The sample reference is obtained from learned user reference 206.

Match filter 300 provides the sum of X multiplied by $C_n$ where X is the value of a particular data sample in the signal from digital filter 264 and $C_n$ is a coefficient from the template in learned user reference 206. Match filter 300 operates according to equation 1 in the same manner as does cross-correlation 272.

Match filters have been shown to theoretically provide the best possible improvement in signal-to-noise ratio of any linear filter, and in the presence of Gaussian (normally distributed) noise, provide the best possible improvement of any filter, linear or nonlinear. In practice, however, match filters can often fall short of their theoretical promise. Benefits and problems of match filters are described in Azevedo, Stephen, "Abdominal-Lead Fetal Electrocardiographic R-Wave Enhancement for Heart Rate Determination", *IEEE Transactions on Biomedical Engineering*, Vol. BME-27 No. 5 (May 1980); Cheng, Quin-lan, and Thakorc, Nitish "ECG Pattern Recognition By Relational Matching of Significant Points", *IEEE/Eighth Annual Conference of the Engineering in Medicine and Biological Society*, 288 (1986); Favret, Andrew, "Computer Matched Filter Location of Fetal R-Waves", *Medical & Biological Engineering*, Vol. 6, 467 (1968); and Monds, Fabian C., and Telford, Roger W., "Matched Filter Location of E.C.G. Complexes", Dept. of Electrical and Electronic Engineering, The Queen's University of Belfast.

Because a match filter's performance is not always predictable in practice, heart rate monitor 100 prefixes match filter 300 with digital filter 264, a narrow frequency bandpass filter, to provide a predictable improvement in the S/N ratio during events where the performance of match filter 300 may degrade. The lack of predictability of match filters is discussed in DeVel, Olivier Y., "R-Wave Detection in the Presence of Muscle Artifacts", *IEEE Transactions On Biomedical Engineering*, Vol. BME-31, No. 11 (November 1984).

The output of match filter 300 is a maximum whenever the output of digital filter 264 matches the signal in the learned user reference 206. Peak enhancer 276 operates in the same manner that it does in learn mode. The output of peak enhancer 276 is processed signal 220.

The procedures described in connection with FIG. 6B with reference to learning mode are repeated in normal mode, except that interval judge 292 also considers the contents of learned history 226.

Three signals are output from communication channel 250 and displayed on LCD display 142. These signals are the user's heart rate displayed as a number, a pulse indicator which is used to drive a blinking heart-shaped object on the LCD display that blinks at the user's heart rate, and the performance level. The pulse indicator signal is derived from QRS detector 286 through connector 370. Alternatively, the pulse indicator signal could be derived from the heart rate signal. An advantage of deriving the pulse indicator signal from QRS detector 286 rather than from the heart rate signal is that the pulse from QRS detector 286 has not been averaged and smoothed. By not being derived from an averaged signal, the pulse indicator signal can give the user a faster response time when the user removes his finger from sensor 104A. This feedback teaches the user to keep his finger on sensor 104A.

It will be obvious to those having skill in the art that many changes may be made in the above described details of the preferred embodiment of the present invention without departing from the underlying principles thereof. The scope of the present invention should be determined, therefore, only by the following claims.

We claim:

1. A heart rate monitor that determines a user's heart rate, comprising:
   sensing means for sensing a biosignal and producing a sensed signal;
   signal modifying means for modifying the sensed signal and producing a modified signal;
   characteristic determining means for determining characteristics of a first portion of the modified signal;
   matching means for matching a second portion of the modified signal with the characteristics and producing a matched signal therefrom;
   matched signal modification means for receiving the matched signal and producing a modified matched signal therefrom; and
   heart rate calculating means for receiving the modified matched signal and for calculating the user's heart rate from the modified matched signal.

2. The heart rate monitor of claim 1, wherein the sensing means senses the bio-signal from a wrist and finger of the user.

3. The heart rate monitor of claim 1, wherein the characteristic determining means includes correlating means for correlating the first portion of the modified signal with prestored biosignal data and producing a correlated signal.

4. The heart rate monitor of claim 1, wherein the characteristic determining means includes
   processing means for processing the modified signal to produce a processed signal; and
   parametric screen means for determining whether the processed signal satisfies certain parameters.

5. The heart rate monitor of claim 1, wherein the characteristic determining means includes
   processing means for processing the modified signal to produce a processed signal; and
   adaptive thresholding means for determining whether the processed signal exceeds a threshold.

6. The heart rate monitor of claim 5, wherein the adaptive thresholding means comprises means for reducing the threshold if the processed signal does not exceed the threshold within a predetermined time.

7. The heart rate monitor of claim 1, wherein the heart rate calculating means includes parametric screen means for determining whether the matched signal satisfies certain parameters.

8. The heart rate monitor of claim 1, wherein the heart rate calculating means includes adaptive thresholding means for determining whether the matched signal exceeds a threshold.

9. The heart rate monitor of claim 1, wherein the heart rate calculating means includes:
   detected signal producing means for producing a first detected signal in response to a first section of the matched signal meeting criteria, and producing a second detected signal in response to a second section of the matched signal meeting the criteria; and
   interval judging means for determining the length of time between the first and the second detected signals, and for determining whether the first detected signal represents a heart beat by using the length of time.

10. The heart rate monitor of claim 9, further comprising false negative detecting means for detecting when a portion of the matched signal represents a heart beat but does not meet the criteria.

11. The heart rate monitor of claim 1, wherein the heart rate monitor is of a size that is suitable to be worn on the user's wrist.

12. The heart rate monitor of claim 1, wherein the matching means includes a narrow frequency bandpass digital filter and a match filter.

13. The heart rate monitor of claim 1, wherein the heart rate calculating means includes
   interval information producing means for producing interval period information; and
   momentum machine means for converting the interval period information to heart rate information.

14. The heart rate monitor of claim 13, wherein the momentum machine is a variable depth moving average calculator.

15. The heart rate monitor of claim 13, wherein the interval period information is instantaneous.

16. The heart rate monitor of claim 1, further comprising signal-to-noise ratio determining means for receiving the modified matched signal and for determining a signal-to-noise ratio of a section of the modified matched signal; and performance predicting means for predicting based on the signal-to-noise ratio an approximate length of time that will be required by the heart rate monitor to determine the heart rate.

17. The heart rate monitor of claim 1, wherein the matching means operates in real time.

18. The heart rate monitor of claim 1, further comprising a strap suitable to be worn on a wrist of the user and a container attached to the strap, the container enclosing the characteristic determining means, the matching means, and the heart rate calculating means.

19. The heart rate monitor of claim 1, further comprising performance predicting means for predicting a level of performance of the heart rate monitor.

20. The heart rate monitor of claim 1, further comprising:
   derived property determining means for receiving the modified matched signal and for producing a derived property signal that is indicative of a selected derived property of a section of the modified matched signal; and
   performance predicting means for receiving the derived property signal and producing based on the derived property signal a performance prediction signal that is predictive of a level of performance of the heart rate monitor in determining the heart rate of the user.

21. The performance predictor of claim 20, wherein the level of performance is a level of exercise that the user may engage in while the heart rate monitor accurately determines the heart rate of the user.

22. A performance predictor for a heart rate monitor that determines heart rate of a user, the performance predictor comprising:
   signal-to-noise ratio determining means for receiving a processed biosignal and for producing a signal-to-noise ratio signal that is indicative of a signal-to-noise ratio of a section of the processed biosignal; and
   performance predicting means for receiving the signal-to-noise ratio signal and producing based on the signal-to-noise ratio signal a performance prediction signal that is predictive of an approximate length of time that will be required by the heart rate monitor to determine the heart rate of the user.

23. The performance predictor of claim 22, wherein the performance predicting means produces the performance prediction signal based on a signal that is indicative of a length of time required by the heart rate monitor to learn certain characteristics of the processed biosignal in addition to being based on the signal-to-noise ratio signal.

24. A performance predictor for a heart rate monitor that determines heart rate of a user, the performance predictor comprising:
   means for receiving a processed biosignal and for producing a derived property signal that is indicative of a selected derived property of a section of the processed biosignal; and
   performance predicting means for receiving the derived property signal and producing based on the derived property signal a performance prediction signal that is predictive of a level of performance of the heart rate monitor in determining the heart rate of the user.

25. The performance predictor of claim 24, wherein the performance predicting means producing the performance prediction signal based on a signal that is indicative of a length of time required by the heart rate monitor to learn characteristics of a biosignal of the user in addition to being based on the signal-to-noise ratio signal.

26. The performance predictor of claim 24, wherein the level of performance is an approximate length of time that will be required by the heart rate monitor to determine the heart rate of the user.

27. The performance predictor of claim 24, further comprising a container that is of a size suitable to be worn on the wrist of the user and that contains the performance prediction means, and wherein the heart rate monitor is a wrist worn heart rate monitor.

28. A wrist worn heart rate monitor that determines a user's heart rate, comprising:
   learning means for learning characteristics of a first portion of a processed biosignal of the user;
   matching means for matching a second portion of the processed biosignal with the characteristics to produce a matched signal
   heart rate calculating means responsive to the matched signal for calculating the heart rate of the user;
   display means for displaying the heart rate of the user; and
   a container that is of a size suitable to be worn on the wrist of the user and that contains the learning means and the heart rate calculating means.

* * * * *